United States Patent [19]

Sugiyama et al.

[11] 4,345,091
[45] Aug. 17, 1982

[54] METHOD OF PRODUCING N-BENZYLOXYCARBONYL-L-ASPARTIC ACID

[75] Inventors: Katsumi Sugiyama; Hideo Takeda, both of Kawasaki; Hiroko Sato, Fuchu, all of Japan

[73] Assignee: Ajinomoto Company Incorporated, Tokyo, Japan

[21] Appl. No.: 224,477

[22] Filed: Jan. 12, 1981

[30] Foreign Application Priority Data

Feb. 4, 1980 [JP] Japan ................................. 55-12315

[51] Int. Cl.$^3$ ........................................... C07C 125/06
[52] U.S. Cl. ................................................... 560/163
[58] Field of Search ........................................ 560/163

[56] References Cited

U.S. PATENT DOCUMENTS 3,808,190 4/1974 Dahlmans ..................... 260/112.5
4,293,706 10/1981 Gorman ............................ 560/163

FOREIGN PATENT DOCUMENTS 837071 6/1960 United Kingdom .
1336650 5/1971 United Kingdom .

OTHER PUBLICATIONS

Bergann, Berichte, 65 pp. 1192–1201 (1932).

Primary Examiner—Michael L. Shippen
Attorney, Agent, or Firm—Oblon, Fisher, Spivak, McClelland & Maier

[57] ABSTRACT

The reaction between L-aspartic acid and benzyloxycarbonyl chloride is carried out at a specific pH range, i.e., 12.0 to 13.5, whereby highly pure N-benzyloxycarbonyl-L-aspartic acid can be obtained in high yields, while both the by-production of N-benzyloxycarbonyl-α- or β-L-aspartyl-L-aspartic acid and the decomposition of benzyloxycarbonyl chloride to benzyl alcohol are suppressed.

5 Claims, No Drawings

METHOD OF PRODUCING N-BENZYLOXYCARBONYL-L-ASPARTIC ACID

This invention relates to a method of producing N-benzyloxycarbonyl-L-aspartic acid (referred to hereinafter as 'Z-Asp'), according to which little by-products are formed.

It is well known that an α-L-aspartyl-L-phenylalanine lower alkyl ester (referred to hereinafter as 'α-APA') is useful as sweetening agents.

There have been developed various methods of producing an α-APA. One of these method comprises subjecting L-aspartic acid (referred to hereinafter as 'Asp') to benzyloxycarbonylation, and reacting the Z-Asp, after converted to the corresponding anhydride, with an L-phenylalanine lower alkyl ester (referred to hereinafter as 'PA'). See U.S. Pat. No. 3,786,039.

This method is indeed excellent in its easy operation and its stable reactions, but is defective in that N-benzyloxycarbonyl-α- or β-L-aspartyl-L-aspartic acid (referred to hereinafter as 'Z-AA') is by-produced during the benzyloxycarbonylation. The Z-AA is reacted with a PA in a subsequent step, giving an N-benzyloxycarbonyl-L-aspartyl-L-aspartyl-L-phenylalanine lower alkyl ester. Removal of the benzyloxycarbonyl group (Benzyloxycarbonyl will be referred to hereinafter as 'Z'.) from the last-mentioned ester gives an L-aspartyl-L-aspartyl-L-phenylalanine lower alkyl ester (referred to hereinafter as 'AAPA'). An AAPA is very difficult to remove from an α-APA and, accordingly, an α-APA contaminated by an AAPA is very difficult to purify. An ion-exchange resin has heretofore been indispensable to remove the AAPA impurity from an α-APA contaminated with an AAPA.

In this connection, it is to be noted that, out of APA's, α-L-aspartyl-L-phenylalanine methyl ester (referred to hereinafter as 'α-APM') as sweetening agents has been already put on the market in some countries such as France, Belgium and Luxemburg.

The inventors of this invention have found as a result of their intensive and extensive study that, if the pH where Asp is reacted with benzyloxycarbonylchloride (referred to hereinafter as 'Z-Cl') is being adjusted within a range of 12.0 to 13.5 throughout the reaction time, both the by-production of Z-AA(α) or Z-AA(β) and the decomposition of Z-Cl to benzyl alcohol are suppressed. Such suppression, in turn, means that highly pure Z-Asp can be obtained in high yields. This invention has been completed on the basis of such findings. It would be easily realized from the foregoing that, when an α-APA is produced by the method explained above with reference to U.S. Pat. No. 3,786,039, highly pure α-APA can be obtained in high yields, if Z-Asp obtained in accordance with this invention is used as one of the starting materials.

There are disclosed, e.g., in Berichte 65, 1192 (1932) methods of producing N-benzyloxycarbonyl-amino acids, including Z-Asp, which comprise reacting various amino acids, including Asp, with Z-Cl. According to the Berichte disclosure, sodium hydroxide or magnesium oxide is used in an amount equivalent or nearly equivalent to the combined (a) carboxyl group in the free form of the amino acid and (b) hydrogen chloride to be formed from the Z-Cl, when the reaction is carried out.

When Z-Asp is produced under the Berichte reaction conditions, the pH never reaches such a high value as a value between 12.0 and 13.5 according to this invention, if magnesium oxide is used, and Z-AA is by-produced in larger amounts accordingly. On the other hand, if sodium hydroxide is used, it is thought that the pH is sometimes elevated locally in the reaction mass over the upper limit of the pH range defined by this invention, because there is no idea in the Berichte disclosure of maintaining the pH within a certain range throughout the reaction time. Too high pH values caused locally in the reaction mass, in turn, bring about the useless decomposition of Z-Cl to benzyl alcohol, and Asp remains unreacted in larger amounts accordingly. Even when sodium hydroxide is used, Z-AA is produced in larger amounts as in the case magnesium oxide is used, unless the pH is made sufficiently high.

U.S. Pat. No. 3,808,190 also discloses under Example I (A) the preparation of N-carbobenzoxy-aspartic acid, according to which the pH was maintained at 8-9 first with sodium bicarbonate and then with sodium hydroxide. This prior art never anticipates nor even hints the underlying idea of the specific pH range in accordance with this invention.

By employing the pH condition of this invention, both the by-production of Z-AA resulting from too low pH values and the by-production of benzyl alcohol resulting from too high pH values are suppressed. Z-Asp can be produced in high yields accordingly.

This invention will be explained in greater detail, as follows;

According to this invention, Asp may be used in the free form or in the salt form such as sodium or potassium salt. Furthermore, it need not be in the excessively purified form. It may contain impurities if in such small amounts insufficient to inhibit the reaction, i.e., benzyloxycarbonylation. E.g., crude Asp crystals may be used which have been obtained by adjusting the pH of an Asp fermentation broth after concentrated if necessary to the isoelectric point of Asp, said broth having, in turn, been obtained by a fermentative method with the use of sugars, fumaric acid or the like as raw materials. Asp or its monoalkali or dialkali metal salt crystals or the like may also be used which have been collected from an eluate concentrated and/or adjusted in pH if necessary, said eluate having, in turn, been obtained by passing as Asp fermentation broth through a column of a strongly acidic cation exchange resin and eluting the Asp adsorbed on to the column with aqueous NaOH solution or the like.

Asp or its salt is subjected to benzyloxycarbonylation, usually as its aqueous solution. The solution is adjusted in pH to between 12.0 and 13.5, using sodium or potassium hydroxide or the like. The concentration of Asp in the solution is not critical, but 20 to 45 weight % solutions are usually used. Too dilute solutions cause difficulties such as low separation yields of the aimed-at substance from the reaction mixture. It is desirable that the reaction is carried out in a liquid phase and from this point of view the upper limit of the concentration of Asp in its solution is determined.

Z-Cl may be used as it is, but it is usually used as a solution of it dissolved in an organic solvent which does not interfere with the reaction and is not miscible with aqueous Asp solution. Toluene, EDC or the like may be exemplified as such organic solvent. It is appropriate to use Z-Cl in an amount of about 1.1 times the mole of Asp, in consideration of the decomposition of Z-Cl during the reaction period of time, and in a concentration of 30 to 60 weight %. Too low concentrations cause delayed reaction rates, and, on the other hand, too high concentrations prevent efficient removal with an organic solvent of by-products such as benzyl alcohol from the reaction mixture.

The reaction is carried out e.g., by mixing an Asp solution and a Z-Cl solution. Reaction when carried out at elevated temperatures facilitates the decomposition of Z-Cl, and it is very appropriate that the reaction is carried out at 0° to 30° C.

Sufficient stirring is made during the reaction period, whereby the two solutions are well mixed. The pH of the reaction mass is maintained within a range of 12.0 to 13.5 throughout the reaction period by addition of sodium hydroxide or the like. 2 to 3 hours of the reaction period will suffice.

When the reaction has been finished, Z-Asp, Z-AA, unreacted Asp and the like are present in the aqueous layer, while unreacted Z-Cl, benzyl alcohol resulting from the decomposition of Z-Cl, and the like are present in the organic solvent layer.

Z-Asp is used as it is or after separated and purified, in dependence of its use. One example of separation and purification methods comprises separating the aqueous layer from the organic solvent layer, neutralizing the separated aqueous layer with hydrochloric acid, sulfuric acid or the like, cooling the neutralized aqueous layer, whereby Z-Asp is crystallized out, and separating the Z-Asp crystals. Recrystallization is carried out, if necessary. From the separated aqueous layer, the Z-Asp may also be separated by extracting the ethyl acetate, n-butanol, ketones immiscible with water such as methyl ethyl ketone and methyl isobutyl ketone, and the like combined recrystallization and extraction bring about higher purities.

In accordance with the method of this invention, the by-production of Z-AA, an obstacle to the production of α-APA's, may be suppressed, the racemization of Asp does not take place irrespectively of reaction at elevated temperatures, and highly pure Z-Asp is produced in high yields accordingly. This means that the final substance, i.e., an α-APA can be produced in high yields.

EXAMPLE

L-aspartic acid is dissolved in aqueous NaOH solution to obtain a 36 weight % Asp solution, its pH being within a certain range.

222 g of the solution (containing 0.6M Asp) is put into a four-necked flask of one liter capacity equipped with a stirrer, a thermometer, a pH-meter and a dropping funnel, cooled to 10° C. and then added with 267 g 42 weight % solution of benzyloxycarbonyl chloride in tolulene (containing 0.66 M Z-Cl).

The reaction is carried on at 10°–30° C. for 3 hours, while the pH of the reaction mixture is being maintained within said certain range by addition of aqueous 25% NaOH solution.

The toluene is thereafter removed by layer separation. The aqueous layer is added with 230 g water, adjusted in pH to 1 with 35% hydrochloric acid, and allowed to stand overnight at 5° C.

The resulting Z-Asp crystals are, after collected by centrifugation, washed with water and dried under reduced pressure.

6 runs of the above procedure were carried out with various pH ranges.

The results are listed in Table 1. Analysis of the impurities was carried out by thin layer chromatography (100 γ spot).

TABLE 1

| Run No. | | 1 | 2 | 3 | 4 | 5 | 6 |
|---|---|---|---|---|---|---|---|
| pH range (not less than ~ less than) | | 8.0 ~ 10.0 | 10.0 ~ 11.0 | 11.0 ~ 12.0 | 12.0 ~ 13.0 | 12.5 ~ 13.5 | 13.5 ~ |
| Yield in mole % of Z-Asp based on Asp | | 68.3 | 79.5 | 78.6 | 87.3 | 86.2 | 80.2 |
| Impurities in Z-Asp crystals (%) | Asp (*1) Z-AA(α) | 3.5 | 3.0 | 1.5 | Trace | Trace | Not detected |
| | (*2) Z-AA(β) | 1.5 | 1.0 | 0.5 | Trace | Trace | Not detected |
| | Asp | 5.0 | 0.2 | 0.3 | 0.6 | 1.0 | 7.5 |
| | Others | Not detected | Not detected | Not detected | Not detected | Not detected | Trace |

*1: N-benzyloxycarbonyl-α-L-aspartyl-L-aspartic acid
*2: N-benzyloxycarbonyl-β-L-aspartyl-L-aspartic acid It would be easily understood from Table 1 that highly pure Z-Asp can be produced in high yields under the reaction conditions of this invention.

What is claimed is:

1. In the process of producing N-benzyloxycarbonyl L-aspartic acid by the reaction of a solution of L-aspartic acid or its sodium or potassium salt with a solution of benzyloxycarbonyl chloride, the improvement consisting essentially in carrying out the reaction while the pH is maintained within the range of 12.0 to 13.5 throughout the reaction.

2. The process of claim 1, wherein the pH is maintained at the range of 12.0 to 13.5 by the addition of sodium hydroxide or potassium hydroxide.

3. The process of claim 2, wherein the reaction is carried out using L-aspartic acid.

4. The process of claim 3, wherein the concentration of L-aspartic acid in the solution is between 20 to 45% by weight.

5. In the process of producing N-benzyloxycarbonyl L-aspartic acid by the reaction of L-aspartic acid or its sodium or potassium salt with N-benzyloxycarbonyl chloride, the improvment consisting essentially in carrying out the reaction by adding the N-benzyloxycarbonyl chloride as such to an aqueous solution of L-aspartic acid while th pH is maintained within the range of 12.0 to 13.5 throughout the reaction.

* * * * *